United States Patent
Ma

(10) Patent No.: US 10,835,271 B2
(45) Date of Patent: Nov. 17, 2020

(54) EMBOLUS REMOVAL DEVICE WITH BLOOD FLOW RESTRICTION AND RELATED METHODS

(71) Applicant: NeuroVasc Technologies, Inc., Laguna Hills, CA (US)

(72) Inventor: Jianlu Ma, Irvine, CA (US)

(73) Assignee: NeuroVasc Technologies Inc., Irvine, CA (US)

( * ) Notice: Subject to any disclaimer, the term of this patent is extended or adjusted under 35 U.S.C. 154(b) by 33 days.

(21) Appl. No.: 16/123,947

(22) Filed: Sep. 6, 2018

(65) Prior Publication Data

US 2019/0000490 A1 Jan. 3, 2019

Related U.S. Application Data

(63) Continuation of application No. 15/433,455, filed on Feb. 15, 2017, now Pat. No. 10,070,878, which is a
(Continued)

(51) Int. Cl.
*A61B 17/221* (2006.01)
*A61F 2/01* (2006.01)
(Continued)

(52) U.S. Cl.
CPC ...... *A61B 17/221* (2013.01); *A61B 17/12109* (2013.01); *A61B 17/12131* (2013.01); *A61F 2/013* (2013.01); *A61M 25/0021* (2013.01); *A61B 90/39* (2016.02); *A61B 2017/00867* (2013.01); *A61B 2017/00893* (2013.01); *A61B 2017/1205* (2013.01);
(Continued)

(58) Field of Classification Search
CPC .............. A61B 7/221; A61B 17/12109; A61B 17/12131; A61B 2017/00867; A61B 2017/2217; A61B 2090/3966; A61B 2017/1205; A61B 2017/22079; A61B 2017/00893; A61M 25/0021; A61M 2025/0042
USPC .................................. 606/159, 200
See application file for complete search history.

(56) References Cited

U.S. PATENT DOCUMENTS

| 2011/0214303 A1 | 9/2011 | Aboytes |
| 2015/0112376 A1 | 4/2015 | Molaei et al. |

FOREIGN PATENT DOCUMENTS

| CN | 101340849 A | 1/2009 |
| WO | WO2009/126747 A1 | 10/2009 |

(Continued)

OTHER PUBLICATIONS

European Search Report dated Apr. 19, 2019 for corresponding European Application No. EP 16 86 0505.
(Continued)

*Primary Examiner* — George J Ulsh
(74) *Attorney, Agent, or Firm* — Raymond Sun

(57) ABSTRACT

A clot removal device has an expandable treatment member having a distal tip and a proximal end, a delivery wire having a distal end coupled to the proximal end of the expandable treatment member, and a flow restrictor carried along the delivery wire at a location that is separate and proximal from the expandable treatment member. The flow restrictor has a body with a distal section and a proximal section, the distal section being covered and the proximal section being uncovered. The expandable treatment member is moveable relative to the flow restrictor, and can be retracted into the distal section.

6 Claims, 7 Drawing Sheets

Related U.S. Application Data continuation of application No. 15/294,708, filed on Oct. 15, 2016, now abandoned.

(51) Int. Cl.
| | | |
|---|---|---|
| *A61B 17/12* | (2006.01) | |
| *A61M 25/00* | (2006.01) | |
| *A61B 90/00* | (2016.01) | |
| *A61B 17/00* | (2006.01) | |
| *A61B 17/22* | (2006.01) | |

(52) U.S. Cl.
CPC ............... *A61B 2017/2212* (2013.01); *A61B 2017/2215* (2013.01); *A61B 2017/2217* (2013.01); *A61B 2017/22038* (2013.01); *A61B 2017/22079* (2013.01); *A61B 2090/3966* (2016.02); *A61F 2002/016* (2013.01); *A61F 2230/0067* (2013.01); *A61M 2025/0042* (2013.01)

(56) References Cited

FOREIGN PATENT DOCUMENTS

| WO | WO2010/014447 A2 | 2/2010 |
| WO | WO2012/156924 A1 | 11/2012 |
| WO | WO2014/008460 A2 | 1/2014 |

OTHER PUBLICATIONS

Office Action dated May 27, 2020 for corresponding China Application No. 201680064144.0.

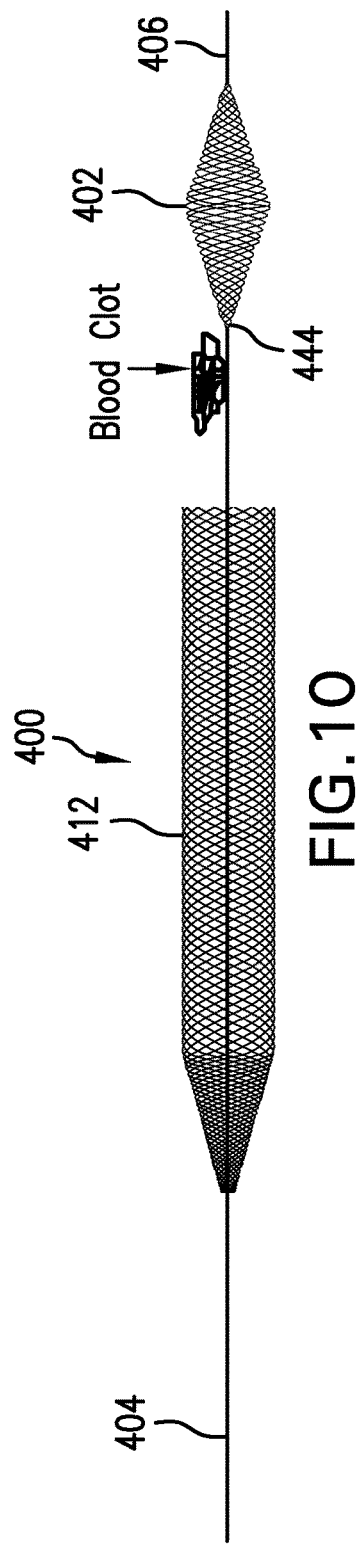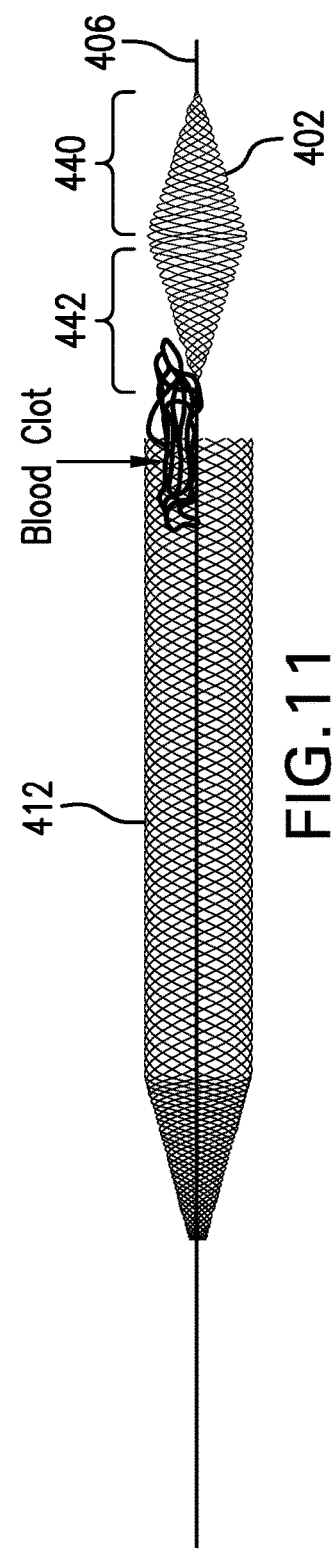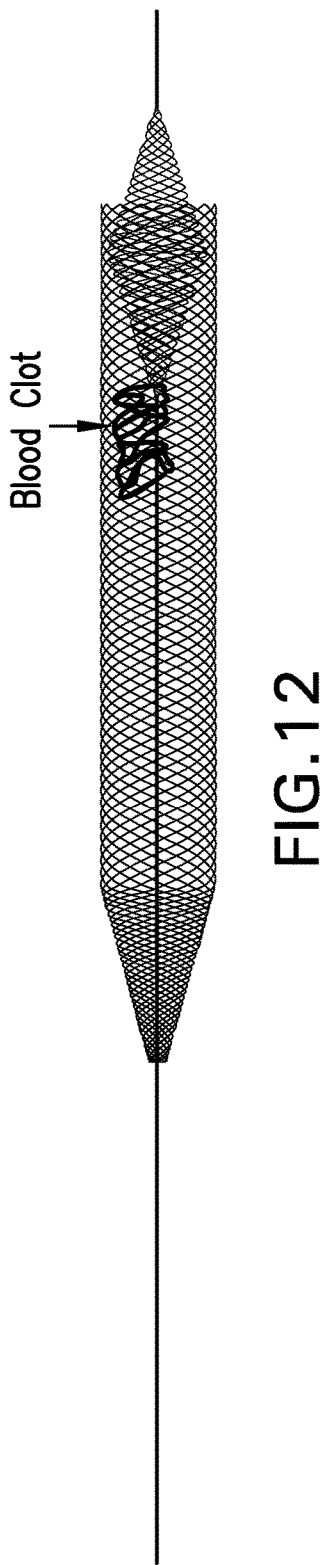

EMBOLUS REMOVAL DEVICE WITH BLOOD FLOW RESTRICTION AND RELATED METHODS

RELATED CASES

This application claims priority from U.S. Provisional Application Ser. No. 62/249,249, filed on Oct. 31, 2015, and U.S. Provisional Application Ser. No. 62/251,069, filed on Nov. 4, 2015, the contents of each of which are incorporated by this reference as if fully set forth herein in their entirety.

BACKGROUND OF THE INVENTION

1. Field of the Invention

The present invention generally relates to devices and methods useful for clot retrieval, and removal devices to treat, among other things, ischemic stroke.

2. Description of the Prior Art

Currently, the FDA-approved treatment options for an acute ischemic stroke include intravenous (IV) delivery of clot dissolving medicine and mechanical thrombectomy.

For treatment use, clot dissolving medicine, such as the thrombolytic agent (Tissue Plasminogen Activator (t-PA)), is injected into the vasculature to dissolve blood clots that are blocking blood flow to the neurovasculature. Intravenous t-PA is currently limited in use because it must be used within a three-hour window from the onset of a stroke and can result in an increased risk of bleeding. This standard of care leaves room for upgrade, and is only the appropriate approach to treatment for a limited class of individuals, groups and temporally-limited exigent cases.

A second option includes the use of mechanical thrombectomy devices. Such devices are designed to physically capture an embolus or clot, and to remove it from the blocked vessel, thereby restoring blood flow. The major advantage of the mechanical thrombectomy device is it can expand the treatment window from three hours to over ten hours.

Some existing mechanical thrombectomy devices used for increasing blood flow through an obstructed blood vessel include: 1) a filter trap designed and built to collect and remove emboli; 2) a cork-screw guidewire-like device to retrieve embolus; and 3) a stent-like device connected to a delivery wire to retrieve embolus. All of these devices suffer from certain disadvantages.

First, filter-type thrombectomy devices tend to be cumbersome and difficult to deliver and deploy, and a larger-profile guide catheter may be needed to fully remove the embolus. In addition, it is difficult to coordinate precise and predictable movement to position the device properly in the vessel. The device can drift within the vessel, twist, or not be adequately conforming to the vessel wall and, therefore not effective for removing embolus.

Cork-screw guidewire devices can only capture and remove emboli that are firm, or subject to certain mechanical variables such as being held together by itself as one piece. Cork-screw guidewire devices are not effective in removing particulate matter that may be scattered or broken up.

Stent-like mechanical thrombectomy devices are not capable of capturing small emboli that break off from a large embolus (if any), and can lead to complications such as the blockage of distal smaller vessels, vessel dissection, perforation, and hemorrhage arising as a result of over-manipulation in the vessel.

The disadvantages common to all of the devices described above include, for example: 1) the device may capture an embolus, but then lose grasp of it and migrate/deposit it incidentally into another area of the neurovasculature, creating the potential for a new stroke in a different part of the neurovasculature; 2) the device is not capable of capturing small embolus breaking off from the larger embolus and preventing it from migrating to a more distal area of the neurovasculature; 3) the relative large device profile prevents these devices from treating the distal smaller diameter vessels; and 4) risk of sICH (symptomatic Intra-cerebral Hemorrhage) after intra-arterial clot removal in acute stroke patients.

Other flaws in the current mechanical thrombectomy designs include poor visibility/radiopacity, lack of variation in the delivery portion to enhance and improve deliverability, and lack of coatings or modified surface textures on the treatment portion to enhance embolus affinity, etc. In conclusion, there is a great need for improved devices, systems, and methods for restoring blood flow through a blood vessel. None of the existing medical mechanical thrombectomy devices address all necessary needs to date.

SUMMARY OF THE DISCLOSURE

The present invention is directed to a method and devices for removing clots, emboli and other luminal blockages from a blood vessel. A clot removal device is provided, having an expandable treatment member having a distal tip and a proximal end, a delivery wire having a distal end coupled to the proximal end of the expandable treatment member, and a flow restrictor carried along the delivery wire at a location that is separate and proximal from the expandable treatment member. The flow restrictor has a body with a distal section and a proximal section, the distal section being covered and the proximal section being uncovered. An access catheter is delivered to a location proximal to a location of a clot or embolus in a blood vessel, and then the clot removal device is delivered through a lumen in the access catheter to the location of the clot or embolus in the blood vessel. The expandable treatment member is expanded at a location that is at or distal to the location of the clot or embolus, and the clot or embolus is caught in, or engaged with, the expandable treatment member. The access catheter is then positioned with respect to the flow restrictor such that the uncovered proximal section is completely covered by the distal end of the access catheter and the covered distal section forms a seal with the distal end of the access catheter, and then aspiration is applied through the access catheter and through the uncovered proximal section to remove the clot or embolus from the blood vessel.

The clot removal device of the present invention can also be used in accordance with another method, where the clot removal device is delivered to a location of a clot or embolus in a blood vessel, the expandable treatment member is expanded at a location that is at or distal to the location of the clot or embolus, the clot or embolus is caught in, or engaged with, the expandable treatment member, the expandable treatment member is withdrawn into the distal section of the flow restrictor, and the expandable treatment member and the flow restrictor are withdrawn from the blood vessel.

The devices of the present invention can be made from either metallic biocompatible material (such as Nitinol, stainless steel, Co—Cr base alloy, Ta, Ti, etc.) or polymer based biocompatible material (polymers with shape memory effect, PTFE, HDPE, LDPE, Dacron, Polyester, etc.). For ischemic stroke treatment, the expandable treatment member must be flexible enough to negotiate the torturous vasculature of the brain and without modifying the vessel profile at the target location. The profile of the expandable treatment member must be small enough to reach target treatment site as known to artisans.

BRIEF DESCRIPTION OF THE DRAWINGS

FIG. 10 is a side view of a fully expanded clot removal device according to a fourth embodiment of the present invention, FIG. 11 is a side view of the removal device of FIG. 10 showing the expandable treatment member being pulled into the proximal flow restrictor with the clot engaged on its outer surface.

FIG. 12 is a side view of the removal device of FIG. 10 showing the expandable treatment member inside the proximal flow restrictor.

DETAILED DESCRIPTION OF THE PREFERRED EMBODIMENTS

Figure 1:
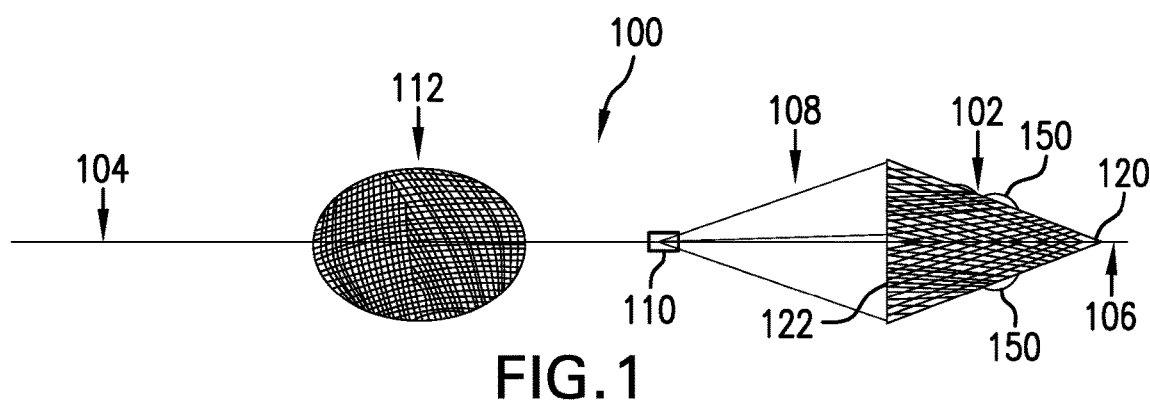
FIG. 1 is a side view of a fully expanded clot removal device according to a first embodiment of the present invention.

The following detailed description is of the best presently contemplated modes of carrying out the invention. This description is not to be taken in a limiting sense, but is made merely for the purpose of illustrating general principles of embodiments of the invention. The scope of the invention is best defined by the appended claims.

The present invention is directed to a device for removing emboli and other luminal blockages. The device includes an expandable treatment member, such as a mesh or a cage, that is associated with a proximal flow restrictor. During treatment, the expandable treatment member is positioned within or distal to an embolus within a blood vessel and then transitioned into an expanded state. In certain embodiments, the expandable treatment member's normal state is the expanded configuration, and the expandable treatment member is compacted and delivered to the treatment site in the compacted configuration through a delivery sheath or catheter. The expandable treatment member is deployed from the delivery sheath, which causes it to return to its normal expanded profile by the elastic energy stored in the device. Expansion of the expandable treatment member engages the expandable treatment member with the emboli or clot at the blockage. In addition, the proximal flow restrictor can also expand to a larger diameter state when it is deployed from the delivery sheath or catheter. Expansion of the proximal flow restrictor advantageously limits or restricts forward blood flow and creates a pressure gradient within the blood vessel between locations distal and proximal to the flow restrictor. The pressure gradient helps to prevent the clots from being flushed away from the treatment member, thereby assisting in removal of the embolus from the blood vessel. Specifically, the pressure difference can act like a vacuum to assist in removal of the embolus from the blood vessel. After expansion, the expandable treatment member and the emboli engaged with the expandable treatment member are removed from the blood vessel. During clot removal, the expandable treatment member (with the blood clot engaged) can also be pulled inside the proximal flow restrictor first (i.e., the clot retrieval component with clots engaged are housed inside proximal restrictor), and then pulled back into guide catheter, and removed from the blood vessel. Furthermore, aspiration/vacuum suction can be applied through the lumen of the access catheter lumen and proximal flow restrictor to prevent clots from breaking off and flowing downstream.

In addition, the proximal flow restrictor regulates the forward blood flow and allows the controlled (gradual) restoration of the blood flow, and reduces the risk of sICH (symptomatic Intra-cerebral Hemorrhage) after intra-arterial clot removal in acute stroke patients.

Devices of the present invention are suitable for removal of blockages in body lumens, and are particularly well-suited for removal of thrombi, emboli, or atheroma in the vasculature, including those in arteries and veins. It is understood that the dimensions of the device may be modified to suit a particular application. For example, devices of the invention used for treatment of deep vein thrombosis may have a larger cross-section than devices of the invention used for treatment of brain ischemic.

Compared with existing mechanical thrombectomy devices, the unique device design included in this invention has the advantage of providing a proximal flow restriction feature to block the forward flow of blood when the device is deployed during use. This feature can help to eliminate or reduce the risk of flush, or the break-up of the blood clots during the procedure.

Another important advantage provided by the present invention is the central lumen of the proximal flow restrictor can be used or combined with the lumen of the access catheter to apply aspiration/suction force to help with the complete removal of the blood clots in the vasculature.

Thus, the device described in the present invention overcomes the shortcomings of the existing technologies and can be delivered to the target vasculature smoothly, can be retrieved safely, and can remove the entire embolus with fewer passes. In use, the mechanical thrombectomy device described in the present invention can be compacted to a low profile and loaded onto a delivery system and delivered to the target location in the vessel by a medical procedure such as through use of a delivery catheter. The mechanical thrombectomy device can be released from the delivery system when it reaches the target implant site and expanded to its normal expanded profile by the elastic energy stored in the device (self-expandable device).

As for the relative position of the expandable treatment member in relation to the embolus or blood clot, it can either be deployed at the site of the embolus, or deployed distal to the embolus. In dealing with long embolus, the expandable treatment member can also be used to remove the embolus from the proximal portion to the distal portion with multiple passes, until the entire embolus is removed.

Figure 2:
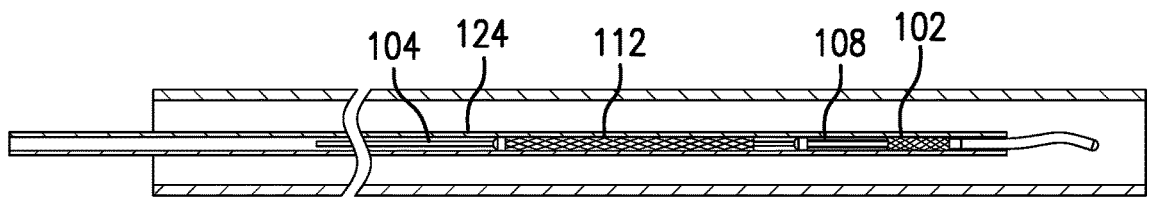
FIG. 2 is a side view of the clot removal device of FIG. 1 shown in a compacted orientation inside a microcatheter.

Turning now to the drawings. FIGS. 1-2 illustrate a device 100 for removing emboli and other luminal blockages according to the present invention. The device 100 can be made from one piece or multiple pieces of Nitinol™ super elastic material or Nitinol™ super-elastic alloy tubing. It can also be made from other biocompatible materials that exhibit super-elastic or shape memory properties. The device 100 can be made by laser cutting, mechanical machining, chemical machining, electrochemical machining, EDM, braiding and related techniques known to those skilled in the art.

The device 100 has an expandable treatment member 102 carried along a delivery wire 104 adjacent the distal end of the delivery wire 104. The delivery wire 104 has a soft distal tip 106 that extends distal from the expandable treatment member 102, and has a marker coil embedded therein. A plurality of laser cut control arms 108 couple the proximal portion of the expandable treatment member 102 with a hub 110 along the delivery wire 104. Specifically, each control arm 108 has opposite ends connecting the proximal portion of the expandable treatment member 102 and the hub 110. A proximal flow restrictor 112 is carried on the delivery wire 104 proximal to the hub 110. Marker bands or marker coils can be incorporated into the proximal flow restrictor 112 and the expandable treatment member 102 for visibility. At least one end of the proximal flow restrictor 112 can move freely along the delivery wire 104.

The expandable treatment member 102 can be configured to act as a catch basket for the clot or embolus, and in this embodiment is shaped as a cone in its fully expanded configuration, with an apex 120 at the distal-most portion of the expandable treatment member 102 secured to the delivery wire 104 adjacent the distal tip 106, and with the expandable treatment member 102 increasing radially in diameter until reaching its proximal-most ring 122. The expandable treatment member 102 can be made of a Nitinol™ braided mesh and can be shape-set to the cone shape by a thermal mechanical process. Most significantly, the expandable treatment member 102 is not cylindrical in configuration which allows it to better conform to the vessel contour and to move more freely inside the vessel. The size of the opening for the ring 122 can range from 0.5 mm to 12 mm. The length of the distal cone portion from the apex 120 to the ring 122 can range from 2 mm to 40 mm.

The meshed frame of the expandable treatment member 102 can be provided with a plurality of openings. Frame members or struts form the body of the meshed frame and define the plurality of openings. In certain embodiments, the frame members are a plurality of intersecting wires or other threads. The frame members may form a mesh or cage-like structure that defines the plurality of openings. In certain embodiments, the expandable treatment member 102 can include a plurality of protrusions 150 on the frame. See FIG. 1 The plurality of protrusions 150 further engages the embolus for removal.

As an alternative to, or in addition to, the plurality of protrusions 150, the expandable treatment member 102 may include one or more surface modifications or treatments. For example, as explained in greater detail below, the surface of the expandable treatment member 102 may be roughened to improve clot adhesion. The main geometrical axis of the expandable treatment member 102 can be offset or different from the longitudinal center axis of the native blood vessel. When the expandable treatment member 102 is in use, both the delivery catheter (e.g., microcatheter 124) and/or the movement axis of the expandable treatment member 102 can be different from the longitudinal central axis of the vessel, and can contact the side wall of the blood vessel.

The delivery wire 104 can be made of super-elastic Nitinol wire, stainless steel wire, braided stainless steel wire, Co—Cr alloy and other biocompatible materials. The diameter of the delivery wire 104 can range from 0.008" to 0.030", and the delivery wire 104 can have variable diameters/stiffness along its length.

This distal tip 106 can be made of Ta, Pt, W, Pt—W, or Pt—Ir alloys for radiopacity, and from radiopaque coils or markers.

The control arms 108 can be laser-cut from a super-elastic Nitinol material. They are preferably taut when the expandable treatment member 102 is in its full expanded configuration. The control arms 108 function to control the opening diameter of the ring 122, so that the largest diameter of the ring 122 can be achieved when the control arms 108 are completely pushed out of the sheath of a microcatheter 124 (see FIG. 2). The diameter of the ring 122 can be adjusted by the length of the control arms 108 being pushed out of the microcatheter 124. Even though the present embodiments are being described as having three control arms 108, it is possible to provide one, or more than two, control arms 108.

The hub 110 can be made from radiopaque materials, and can move freely along, and with respect to, the delivery wire 104. The hub 110 can also be secured to a fixed location along the delivery wire 104

The proximal flow restrictor 112 can be a bulbous structure and can be made of a Nitinol™ mesh, and it is fixedly connected to the delivery wire 104 at its proximal end, while the distal end of the proximal flow restrictor 112 can move freely along, and with respect to, the delivery wire 104. In another embodiment, the proximal flow restrictor 112 can be fixedly connected to the delivery wire 104 at its distal end, while the proximal end of the proximal flow restrictor 112 can move freely along, and with respect to, the delivery wire 104. The proximal flow restrictor 112 can have a first smaller compacted profile for delivery through the microcatheter 124 possible. The proximal flow restrictor 112 can have a second larger expanded diameter/profile when released from the microcatheter 124 or other delivery system to block, limit, or restrict the blood flow. The bulbous structure can be a braided or laser cut structure, and made from a film, membrane, braided or netted material. In certain embodiments, the proximal flow restrictor 112 is a polymeric film or membrane. In other embodiments, the proximal flow restrictor 112 is a braided or woven net formed from a metal, polymer, or combination thereof. The type and material of the proximal flow restrictor 212 may be chosen based on the desired coverage (i.e. amount of flow to be restricted). The surface of the proximal flow restrictor can be either entirely or partially covered by some polymer materials to restrict the blood flow. It can be fabricated from the one or two element(s) of the device 100, or fabricated from other pieces of material, then attached to the delivery wire 104 by mechanical means, or via a thermal (laser or soldering) process, or adhesive/glue, or heat shrink technology. The bulbous structure can also be fabricated from the same piece of Nitinol™ tubing as that of the device 100 by laser cutting or chemical processes and then shape-set to a larger diameter than the raw Nitinol™ tubing.

The proximal flow restrictor 112 can have a diameter in its fully expanded configuration that is about the same as the diameter of the opening ring 122 of the expandable treatment member 102 when the expandable treatment member 102 is in its fully expanded configuration. The diameter of the proximal flow restrictor 112 can range from 0.5 mm to 12 mm, and its length can range from 2 mm to 60 mm.

Radiopaque markers can be attached on any portion of the device 100 for positioning. One way to provide full visibility for the device 100 is to run a radiopaque material through the entire or partial lumen of the delivery wire 104. Markers can also be placed on the expandable treatment member 102 to aid in positioning. In addition, radiopaque markers (marker coils, marker bands, radiopaque wire(s), radiopaque coatings, etc.) can be integrated into the proximal flow restrictor 112.

The device 100 can have a surface treatment on selected portions to improve performance for the selected portions of the device 100. Both the proximal flow restrictor 112 and the expandable treatment member 102 can either be coated or covered, entirely or partially, by typical biocompatible materials for lubricity. The surface of the expandable treatment member 102 can have either a positive or negative charge for improved clot adhesion. The surface of the expandable treatment member 102 can also be either mechanically or chemically treated to have a "rough" surface for improved clot adhesion. The "rough" surface can be achieved by (i) a porous surface coating or layer (ii) a micro blasted surface or micropinning, or (iii) an irregular strut geometry or arrangement.

The expandable treatment member 102 can be fully or partially coated with chemical(s), drug(s) or other bioagents to prevent clotting and/or for the better adhesion between the device and embolus. In addition, the surfaces of the expandable treatment member 102 and the proximal flow restrictor 112 can be treated to form different surface layers (e.g., oxidation layer, Nitro or carbonized or N—C-combined surface layer, etc.) for better adhesion between the expandable treatment member 102 and the embolus.

FIG. 2 shows the device 100 compressed and fitted inside a microcatheter 124. In use, a guide wire can be inserted through the vasculature to the target treatment site, and then the microcatheter 124 is delivered over the guide wire to a target location in a vessel with the device 100 housed therein using conventional delivery techniques that are known to those skilled in the art. Alternatively, the microcatheter 124 can be inserted over the guide wire first, then the compacted device 100 can be inserted through the inner lumen of the microcatheter 124. The distal end of the microcatheter 124 can be positioned proximal to, or inside, or distal to, the clot or embolus at the target location, and there is no need for the microcatheter 124 to traverse the clot or embolus, thereby minimizing the possibility of pushing the clot or embolus downstream in the vessel.

Figure 3A:
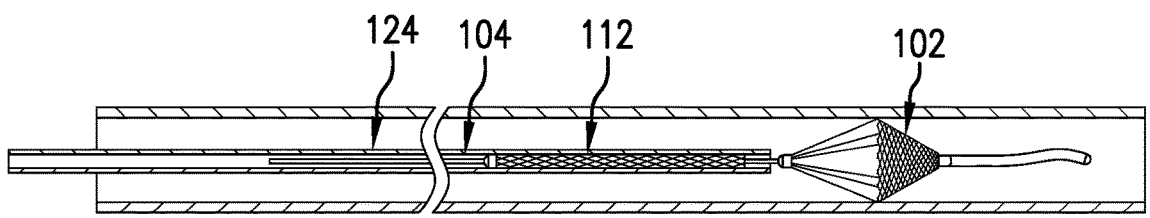
FIG. 3A is a side view of the clot removal device of FIGS. 1 and 2 shown with the expandable treatment member fully pushed outside the microcatheter.
Figure 3B:
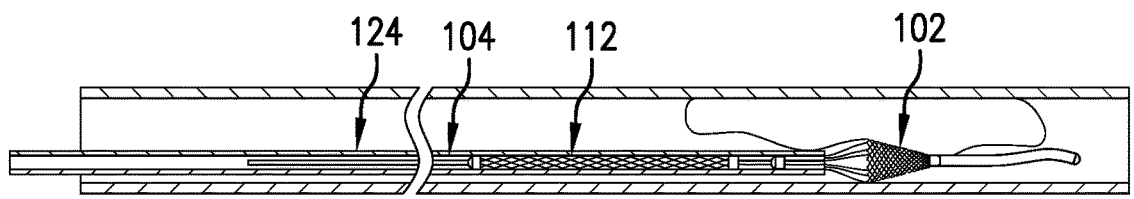
FIG. 3B is a side view of the clot removal device of FIGS. 1 and 2 shown with the control arms and the expandable treatment member slightly pushed outside the microcatheter.

The microcatheter 124 can then be pulled back (proximally) to expose first the expandable treatment member 102 (see FIG. 3A), then the control arms 108, and then later on the proximal flow restrictor 112. Before the control arms 108 are fully exposed, the expandable treatment member 102 will not reach its full diameter, which makes it possible for the expandable treatment member 102 to not disturb clots before the device 100 reaches its desired position. Instead of pulling back the microcatheter 124, it is also possible to deploy the expandable treatment member 102 by inserting the device 100 into the microcatheter 124 until the distal tip 106 reaches the distal end of the microcatheter 124, and then holding the proximal end of the microcatheter 124 in a stationary position, pushing the device 100 distally out of the microcatheter 124. Under this alternative, there is no need to withdraw the microcatheter 124, which allows the positioning to be more accurate. The expandable treatment member 102 will not fully deploy (i.e., reach its largest diameter) until the control arms 108 have been completely pushed out of the microcatheter 124. This allows for a gap, volume, or space (see FIG. 3B) between the expandable treatment member 102 and the actual clot in the vessel, so that the clot will not be pushed downstream and dislodged by the expandable treatment member 102 when the expandable treatment member 102 is pushed out of the microcatheter 124 and located distal to the clot. Once the control arms 108 have been completely pushed out of the microcatheter 124, then the expandable treatment member 102 will reach its full diameter to catch the clot from the distal side of the clot. At this point, the microcatheter 124 and the elongated delivery wire 102 will be pulled back or withdrawn at the same time to remove the clot.

During this procedure, the proximal flow restrictor 112 eliminates or reduces the forward blood flow to minimize the risk of poor clot retention and clot dislodgement. The expandable treatment member 102 can collect all the clots/emboli to prevent them from flowing downstream. The proximal flow restrictor 112 also regulates the flow of blood during and immediately after the procedure to eliminate the effect of sICH for a better clinical outcome.

In other embodiments, the proximal flow restrictor can surround (i) an outer surface or diameter of a proximal portion of the expandable treatment member, or (ii) both the inner and outer surfaces or diameters of the proximal portion of the expandable treatment member. In these embodiments, the proximal flow restrictor can cover a length extending between (i) a proximal end of the expandable treatment member to about half of the length of the expandable treatment member, or (ii) between a proximal end of the expandable treatment member to about one-quarter of the length of the expandable treatment member.

Figure 4:
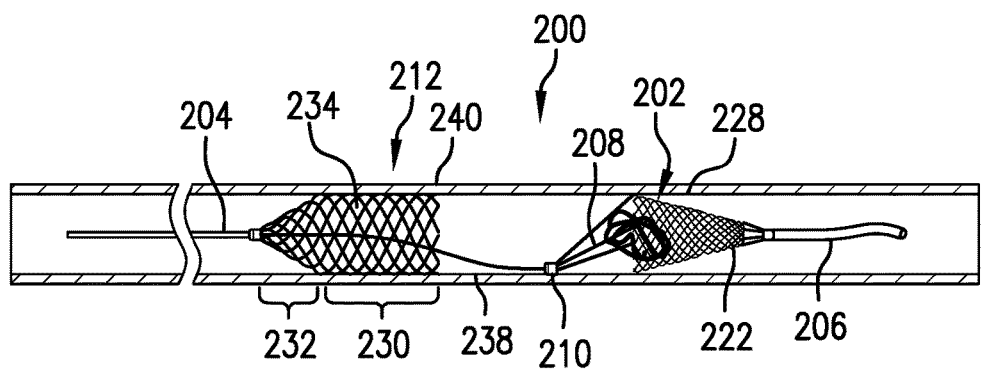
FIG. 4 is a side view of a fully expanded clot removal device according to a second embodiment of the present invention.
Figure 5:
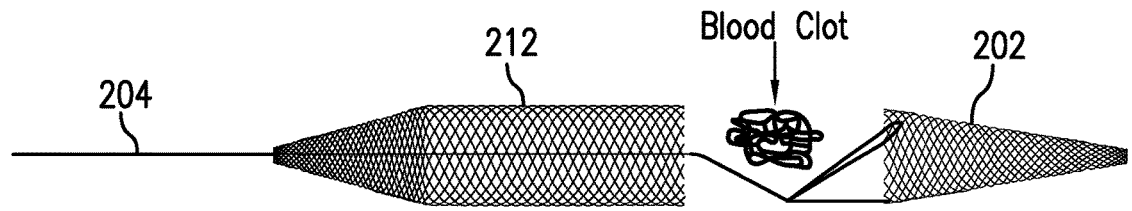
FIG. 5 is a side view of the clot removal device of FIG. 4 showing the collection of a clot in a vessel.
Figure 6A:
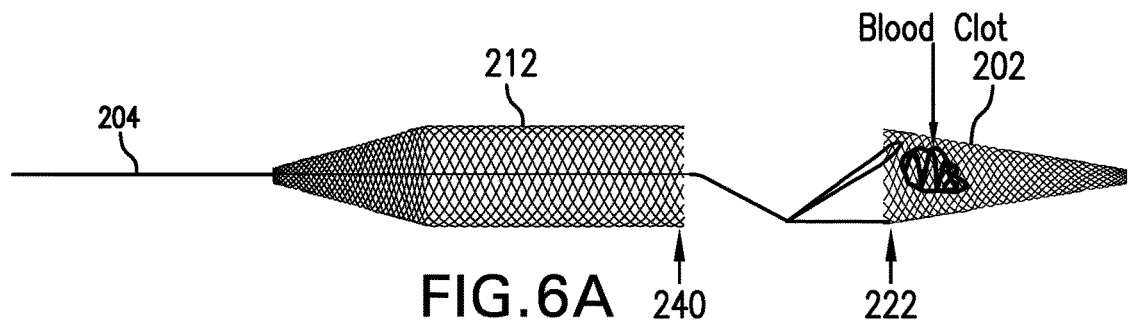
FIG. 6A is a side view of the clot removal device of FIG. 4 showing the clot collected inside the expandable treatment member.
Figure 6B:
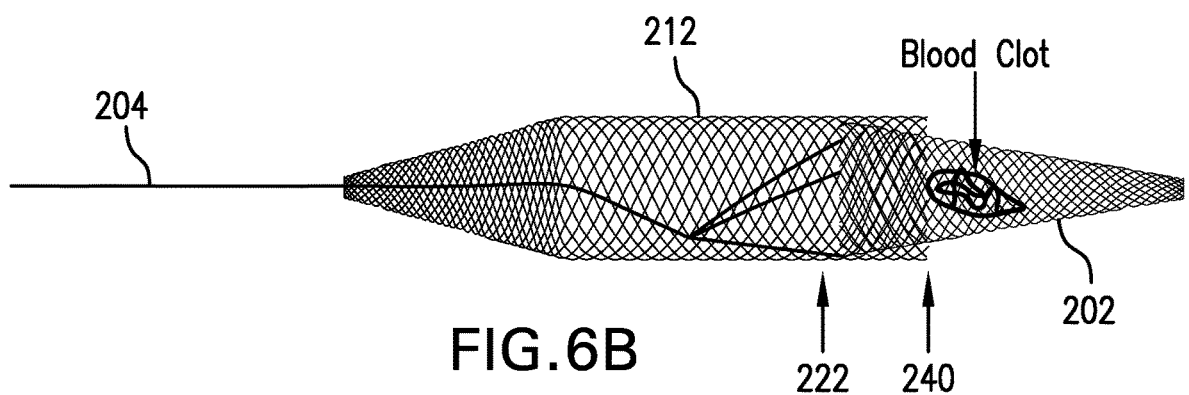
FIG. 6B is a side view of the clot removal device of FIG. 4 showing the clot collected inside the expandable treatment member, and the expandable treatment member inside the proximal flow restrictor.

For example, FIGS. 4-6 illustrate another embodiment of a device 200 for removing emboli and other luminal blockages. The device 200 also has an expandable treatment member 202, a soft distal tip 206 (with marked coil), a delivery wire 204, control arms 208, a hub 210 and a proximal flow restrictor 212 that correspond to the expandable treatment member 102, soft distal tip 106 (with marked coil), delivery wire 104, control arms 108, hub 110 and proximal flow restrictor 112, respectively, for the first embodiment, except for a few differences.

First, the expandable treatment member 202 has a slightly different configuration. Instead of the conical configuration of the expandable treatment member 102, the expandable treatment member 202 has a frusto-conical body 228 where its distal-most end does not terminate in an apex, but has a small distal opening.

Second, the proximal flow restrictor 212 has a different configuration, having a body that includes a cylindrical distal section 230 and a generally conical (or frusto-conical) proximal section 232 that has a tapering configuration. The two sections 230 and 232 combine to define a receiving section.

The body 228 and the sections 230 and 232 can all be laser cut from the same material (e.g., a Nitinol™ tubing or sheet), but the sizes of the cells or openings 234 in the body 228 and the sections 230 and 232 can be varied to vary the flexibility of the different body 228 or sections 230, 232. The section 232 can have an annular distal edge 240 that functions as an open mouth. The sections 230 and 232 can also have different size/porosity, and can either be covered by a biocompatible polymer or left uncovered. One example is to leave the section 232 uncovered, while covering section 230. The uncovered section 232 can be incorporated with other access catheters to facilitate the aspiration/suction function. The proximal flow restrictor 112 can have a braided configuration.

Third, the delivery wire 204 can have a deflected section 238 extending distally from the section 230 at an angle with respect to the central longitudinal axis to the hub 210, which is offset from the central longitudinal axis occupied by the delivery wire 204. In this regard, the control arms 208 extend from the hub 210 towards the body 228 at different angles. The different angles allows the expandable treatment member 202 to navigate the vascular anatomy more easily, and also better facilitates the collection of clots and particles by the expandable treatment member 202. In addition, the different angles for the control arms 208 allow the proximal opening of the expandable treatment member 202 to remain open, and not to collapse, during the procedure. The different angles also makes it easier for the control arms 208 to control the diameter or staged deployment of the expandable treatment member 202 during the procedure.

The proximal flow restrictor 212 is configured so that it can experience relative movement with respect to the expandable treatment member 202. This is accomplished by not having a fixed connection between the proximal flow restrictor 212 and the delivery wire 204, and by allowing the proximal flow restrictor 212 to slide along the delivery wire 204. In other words, the expandable treatment member 202 can move independent of the proximal flow restrictor 212. This provides a more effective capture and removal of the clot as described below.

In use, the device 200 is loaded inside a microcatheter 124, which is delivered to a target location in a vessel with the device 200 housed therein using conventional delivery techniques that are known to those skilled in the art. The distal end of the microcatheter 124 can again be positioned proximal to, or inside, the clot or embolus at the target location, and there is no need for the microcatheter 124 to traverse the clot or embolus. The device 200 can then be pushed distally out of the distal end of the microcatheter 124 to expose first the expandable treatment member 202 and then later on the proximal flow restrictor 212. See FIG. 5. The device 200 is then pulled back or withdrawn so that the expandable treatment member 202 catches the clot. See FIG. 6A. When the delivery wire 204 is pulled back and the expandable treatment member 202 is pulled back with it, the proximal flow restrictor 212 can stay at the same location within the vessel, so that when the annular distal edge 240 of the proximal flow restrictor 212 contacts the annular proximal edge or ring 222 of the body 228, and further proximal pulling of the delivery wire 204 will cause the expandable treatment member 202 to be pulled back into the cylindrical section 230 so that the entire device 200 is removed from the vessel. As a result, the entire clot or embolus can be retained inside a cage defined by the expandable treatment member 202 and the proximal flow restrictor 212 during removal so as to prevent dislodgement or disengagement of the clot. See FIG. 6B. The expanded diameter of the annular proximal edge 222 is preferably slightly smaller than the expanded diameter of the cylindrical section 230 and its annular proximal edge 240 so that the expandable treatment member 202 can be retained inside the cylindrical section 230.

In addition, it is possible to provide the delivery wire 204 with a lumen that opens at an opening that is located inside the proximal flow restrictor 212 (see FIGS. 13-14 below), so that suction can be applied from the proximal end of the access guide catheters or microcatheter 124 to pull smaller clots and particles into the proximal flow restrictor 212 using suction force, and then removed from the vessel.

Finally, the suction/aspiration action through the lumen of the access devices and the encapsulation of the expandable treatment member 102 (with clot engaged) can happen either simultaneously or in sequence during the procedure.

Figure 7:
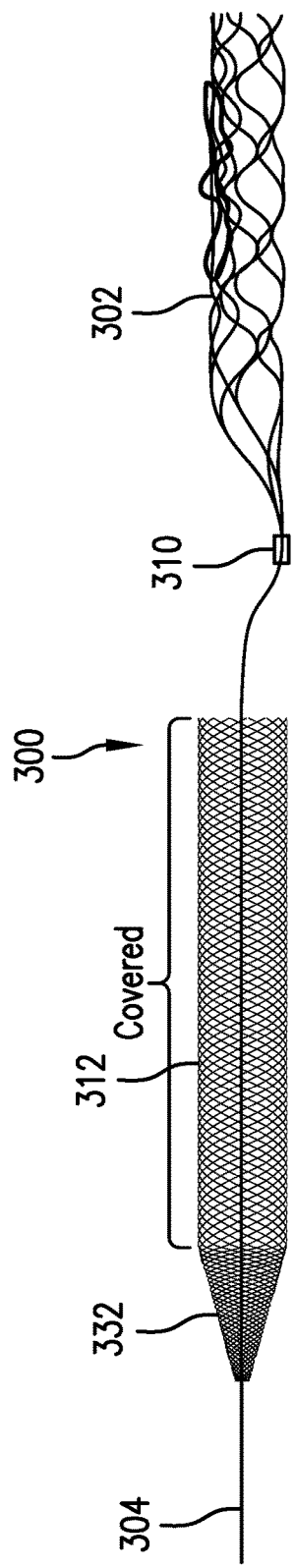
FIG. 7 is a side view of a fully expanded clot removal device according to a third embodiment of the present invention shown with a clot caught on the surface of, and between the cell spaces, of the expandable treatment member.
Figure 8:
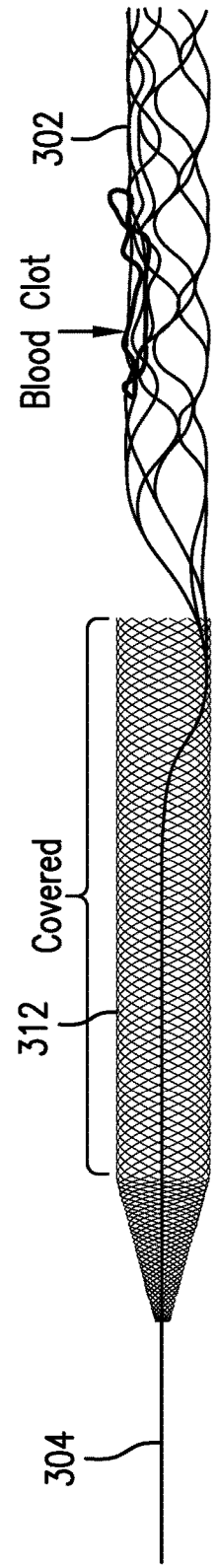
FIG. 8 is a side view of the clot removal device of FIG. 7 showing the expandable treatment member being pulled into the proximal flow restrictor.
Figure 9:
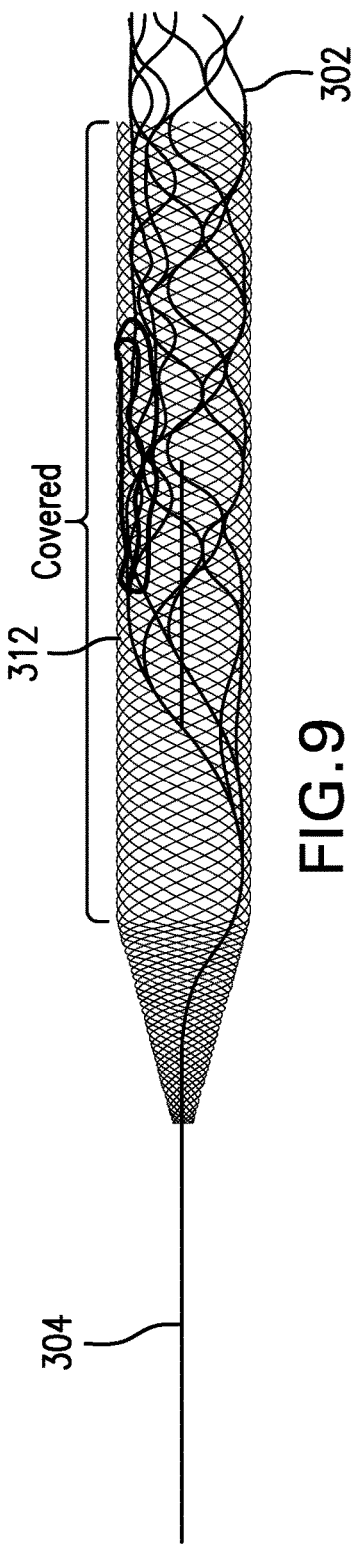
FIG. 9 is a side view of the clot removal device of FIG. 7 showing the expandable treatment member inside the proximal flow restrictor.

FIGS. 7-9 illustrate another embodiment of a device 300 for removing emboli and other luminal blockages. The device 300 is similar to the device 200 in that it also has an expandable treatment member 302, a delivery wire 304, a hub 310 and a proximal flow restrictor 312 that correspond to the expandable treatment member 202, delivery wire 204, hub 210 and proximal flow restrictor 212, respectively, for the second embodiment, except for a few differences.

First, the expandable treatment member 302 has a different configuration, and can be configured as any of the removal devices disclosed in co-pending United States Publication No. 2015-0150672, filed Jan. 16, 2015, whose entire disclosure is incorporated by this reference as if set forth fully herein. For this reason, there are no control wires 108/208.

Second, the proximal flow restrictor 312 can be essentially the same as the proximal flow restrictor 212 in FIGS. 4-6.

Third, the hub 310 can function as a marker or stopper. During the procedure, when the expandable treatment member 302 is being pulled back, the expandable treatment member 302 will start to pull the proximal flow restrictor 312 with it once the hub 310 reaches and engages the proximal end of the inside of the proximal flow restrictor 312. At this stage, the entire (or portion of) expandable treatment member 302 with its collected clot would already be retained inside the proximal flow restrictor 312. Again, suction force can be applied from the proximal end of the access guide catheter or microcatheter to help pull all the clots/emboli inside the proximal flow restrictor 312.

Again, the body of the expandable treatment member 302 and the sections of the proximal flow restrictor 312 can all be laser cut from the same material (e.g., a Nitinol™ tubing or sheet), but the sizes of the cells or openings in the expandable treatment member 302 and the proximal flow restrictor 312 can be varied to achieve varying flexibilities. The proximal tapered portion on the proximal flow restrictor 312 can be uncovered, while the straight portion of the proximal flow restrictor 312 can be covered, to achieve the desired suction effect and suction control.

As shown in FIG. 7, the clot can be caught on the surface of, and between the cell spaces, of the expandable treatment member 302, and the expandable treatment member 302 pulled inside the proximal flow restrictor 312 (see FIGS. 8-9) completely before the entire system (microcatheter and device 300) is removed from the blood vessel. Since the proximal flow restrictor 312 has no fixed joint with the delivery wire 304, it can remain in a fixed location with respect to the delivery wire 304 and the expandable treatment member 302 so that the expandable treatment member 302 (with the blood clot engaged thereon) can be pulled inside the proximal flow restrictor 312. The expandable treatment member 302 can be pulled into the proximal flow restrictor 312 until the hub 310 (acting as a stopper) contacts the narrowed portion of the proximal section 332 of the proximal flow restrictor 312. The proximal portion of the expandable treatment member 302 has a tapered configuration so that it can fit into the narrowed proximal section 332. At this time, the proximal flow restrictor 312 will move together with the expandable treatment member 302 (and blood clot housed inside) when the delivery wire 304 is pulled out. The device 300 can be pulled inside a guide catheter for removal out of the vessel, or can be removed out of the vessel without being pulled inside a guide catheter first. Again, suction force can be applied from the proximal end of the access guide catheter or microcatheter to help pull all the clots/embolus inside the proximal flow restrictor 312.

FIGS. 10-12 illustrate another embodiment of a device 400 for removing emboli and other luminal blockages. The device 400 is similar to the device 100 in that it also has an expandable treatment member 402, a delivery wire 404, distal tip 406 and a proximal flow restrictor 412 that correspond to the expandable treatment member 102, delivery wire 104, distal tip 106 and proximal flow restrictor 112, respectively, for the first embodiment, except for a few differences.

First, the expandable treatment member 402 has a different configuration, and has a distal section 440 that is essentially the same as the conical body of the expandable treatment member 102. However, the expandable treatment member 402 also has a proximal section 442 that is also conically shaped with an apex 444 at its proximal end and with its largest diameter portion coupled to the largest-diameter portion of the distal section 440. The double tapered configuration of the expandable treatment member 402 allows its distal end to be softer and less traumatic, and also provides a less stiff proximal end, which together allow for easier navigation of the vessel anatomy. The distal expandable treatment portion 402 can be either entirely or partially covered by polymer materials to block the blood flow (flow from distal portion of the vessel to proximal portion of the vessel, so that the aspiration effect from the access catheter and proximal flow restrictor will be more effective).

Second, the proximal flow restrictor 412 can be essentially the same as the proximal flow restrictor 212 in FIGS. 4-6.

Third, there is no hub 110 and no control wires 108/208,

Again, the body of the expandable treatment member 402 and the sections of the proximal flow restrictor 412 can all be laser cut from the same material (e.g., a Nitinol™ tubing or sheet), but the sizes of the cells or openings in the expandable treatment member 402 and the proximal flow restrictor 412 can be varied to achieve varying flexibilities.

The clot can be engaged on the outside of the distal section 442 (see FIG. 11) and the expandable treatment member 402 can be pulled inside the proximal flow restrictor 412 (see FIGS. 11 and 12) completely before the entire system (microcatheter and device 300) is removed from the blood vessel. Since the proximal flow restrictor 412 has no fixed joint with the delivery wire 404, it can remain in a fixed location with respect to the delivery wire 404 and the expandable treatment member 402 so that the expandable treatment member 402 (with the blood clot engaged on its outer surface) can be pulled inside the proximal flow restrictor 412. The aspiration can be applied during the procedure through the lumen of the access catheter or microcatheter and the proximal flow restrictor as well.

Figure 13A:
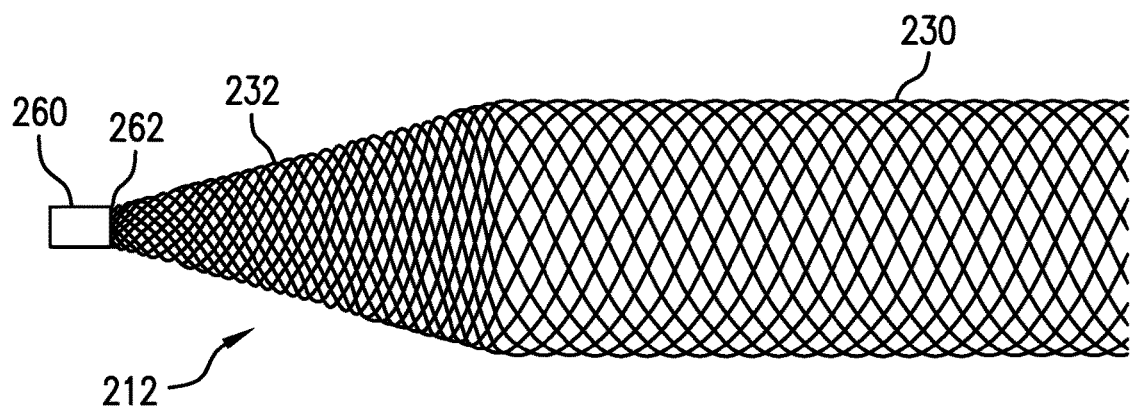
FIG. 13A is an enlarged side view of an exemplary proximal flow restrictor design.
Figure 13B:
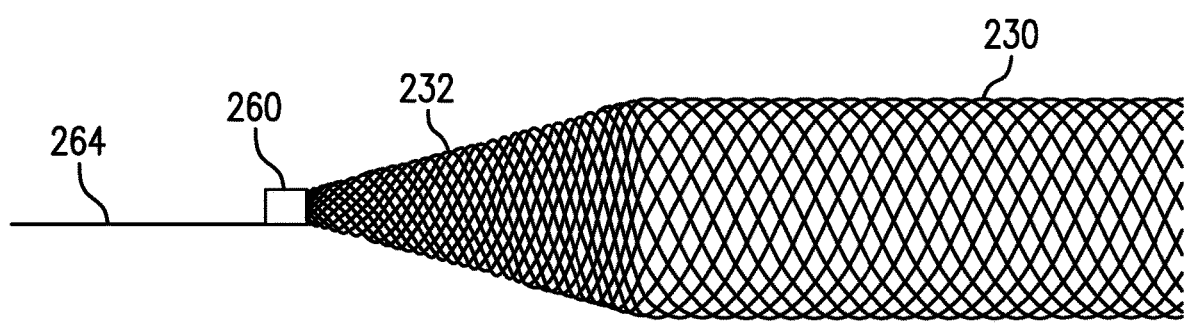
FIG. 13B is an enlarged side view of an exemplary proximal flow restrictor design with a push wire connected from the proximal end.
Figure 13C:
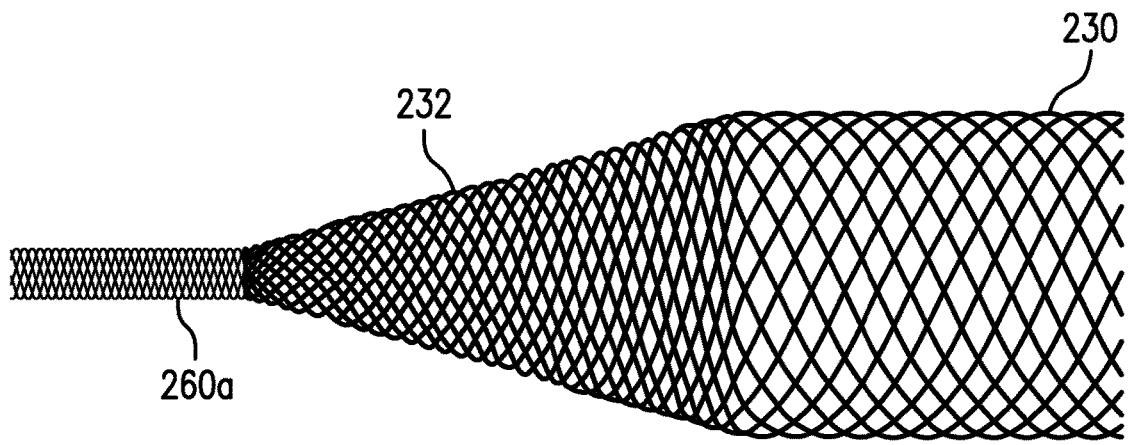
FIG. 13C is an enlarged side view of an exemplary proximal flow restrictor design with a through lumen on the delivery element from the proximal end.

FIGS. 13A, 13B, and 13C show some exemplary design configurations for the braided proximal flow restrictor. The proximal flow restrictor shown in FIGS. 13A-13C and 14A-14B can be the same the proximal flow restrictor 212, although the principles and concepts embodied in FIGS. 13A-13C and 14A-14B also apply to the other proximal flow restrictors shown and described herein.

As shown in FIG. 13B, the proximal flow restrictor 212 can have a central lumen 260 at the proximal end 262, a tapering proximal portion 232, and a cylindrical distal portion 230. The proximal portion 232 can be uncovered, and the distal portion 230 can be covered by biocompatible polymer materials. In use, suction can be applied through the central lumen 260 from the access catheters.

As shown in FIG. 13B, a push wire 264 can be connected to the proximal portion 232 to operate the proximal flow restrictor 212. This design can be used or incorporated with other commercially-available clot removal devices, and can also be used or incorporated with an access catheter, guide catheter, DAC, or microcatheter to apply suction during the clot removal procedure.

As shown in FIG. 13C, a different central lumen structure 260a having a lumen can be connected to the proximal portion 232 to operate the proximal flow restrictor 212. This design can be used or incorporated with other commercially-available clot removal devices, and can also be used or incorporated with an access catheter, guide catheter, DAC, or microcatheter to apply suction during the clot removal procedure.

Figure 14A:
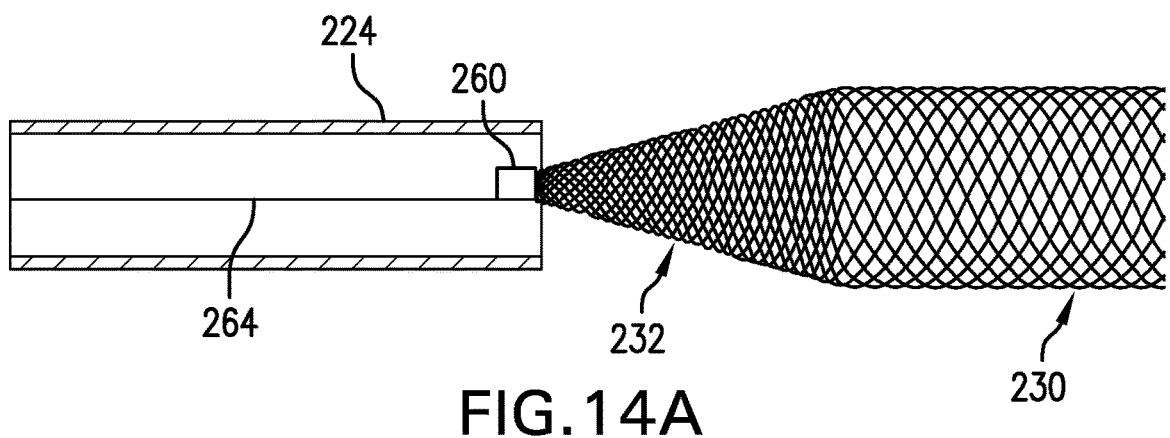
FIG. 14A is an exemplary application of the proximal flow restrictor of FIG. 13B combined with an access catheter, such as a guide catheter, or other procedure support catheters (not in aspiration position).
Figure 14B:
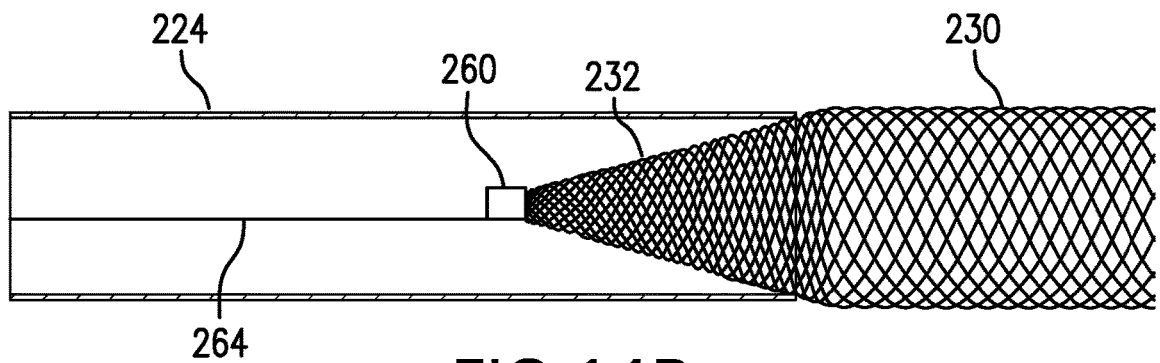
FIG. 14B is an exemplary application of the proximal flow restrictor of FIG. 13B combined with an access catheter, such as a guide catheter, or other procedure support catheters, in an aspiration position.

FIGS. 14A and 14B show an exemplary application of the proximal flow restriction feature. The proximal portion 232 can be fully uncovered or partially uncovered, and the distal portion 230 can be covered by biocompatible polymer materials. In use, the proximal flow restrictor 212 can be delivered to the target location through a microcatheter or other access catheter 224. The proximal central lumen 260 can be used to slide along a guidewire or the push wire 264 of the clot retrieval device. Adjusting the relative position/location of the microcatheter 224 with that of the proximal flow restrictor 212, the proximal flow restrictor 212 can either allow proximal forward flow, or cut off the forward flow. In the situation where forward flow is cut off, the suction effect can be applied through the lumen of the microcatheter 224 for improved clot collection, retention and removal. For example, when the push wire 264 connected to the proximal flow restrictor 212 is pulled back towards the access catheter or microcatheter 224, and the uncovered proximal portion 232 is completely covered by the distal end of the access catheter or microcatheter 224 with the covered distal portion 230 forming a seal with the distal end of the access catheter or microcatheter 224, the forward flow is totally cut off, and then the aspiration/suction can be applied from the proximal end of the access catheter or microcatheter 224 to help retain and collect clots (as shown in FIG. 14B). From FIG. 14B, it is noted that the outer diameter of the access catheter 224 is less than the outer diameter of the fully expanded distal portion 230, but that this seal can still be formed when the proximal end of the distal portion 230 is pulled into the distal opening of the access catheter 224 as the proximal part of the distal portion 230 begins to compress and assume a tapered configuration as the distal portion 230 is pulled into the access catheter 224.

Figure 15A:
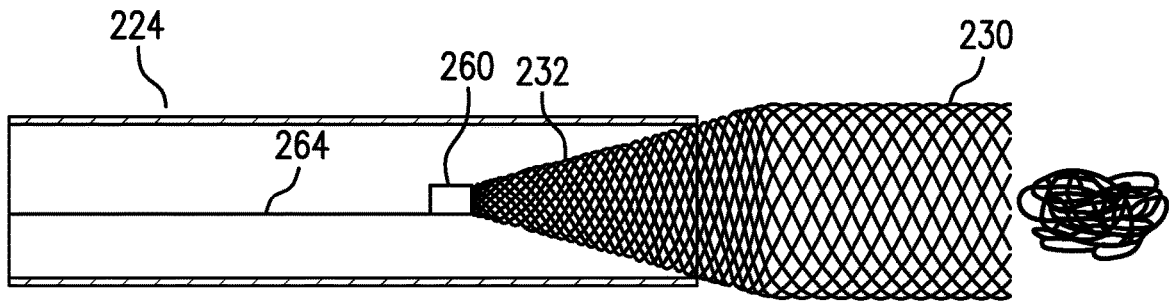
FIGS. 15A-15C illustrate another embodiment of the clot removal device according to the present invention where the expandable treatment member is omitted.
Figure 15B:
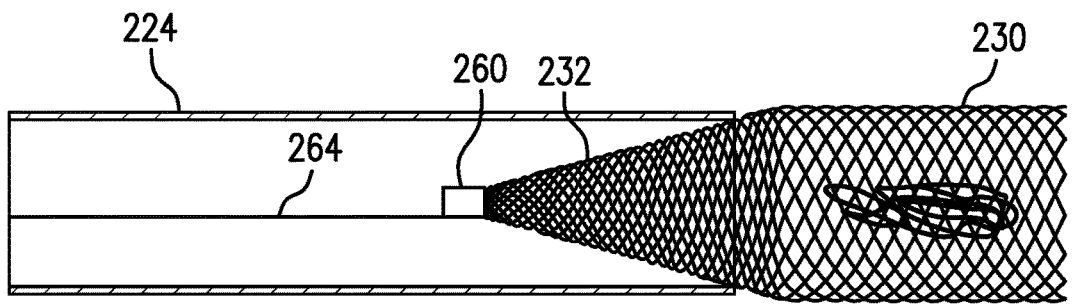
Figure 15C:
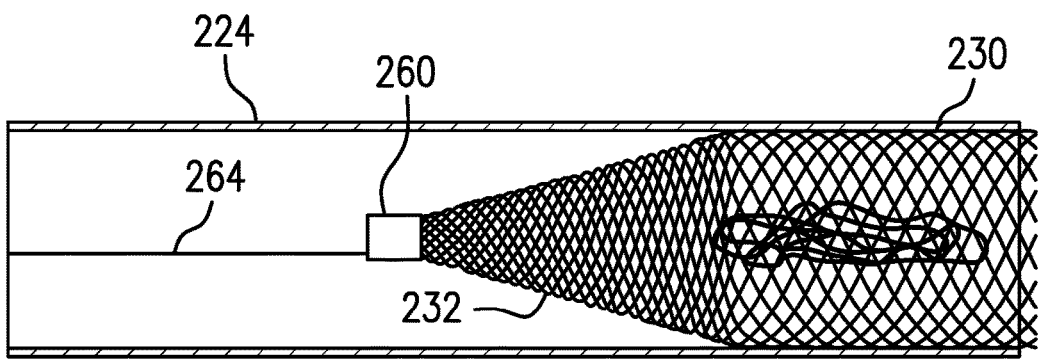

FIGS. 15A-15C illustrate a different embodiment of the present invention, where the device 200 comprises only the flow restrictor 212 and the push wire 264, and where the expandable treatment member 202 is omitted. As shown in FIG. 15A, the distal portion 230 is positioned proximal to the blood clot or embolus, and the relative position/location of the access catheter 224 is adjusted by operating the push wire 264, so that the proximal portion 232 of the flow restrictor is covered by the distal end of the access catheter 224. Aspiration is then applied to the lumen of the access catheter 224 to suction or aspirate the blood clot into the distal portion 230 and/or proximal portion 232 (see FIG. 15B), and then the entire flow restrictor 212 (including the clot inside) is pulled into the access catheter 224 (see FIG. 15C), and the device 200 is removed out of the blood vessel.

As an alternative, if the embodiment shown in FIG. 13C is used, the aspiration can be applied through the central lumen 260a, instead of through the access catheter 224.

Thus, the embodiment of FIGS. 13C and 15A-15C show that the expandable treatment member 202 can be omitted and the flow restrictor 212 itself can be used to remove blood clots or embolus. The structural arrangement of the flow restrictor 212 (uncovered proximal portion 232 and covered distal portion 230) facilitates this type of removal.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. A device for removing a clot or embolus from a blood vessel, comprising:
   an expandable treatment member having a distal tip and a proximal end;
   a delivery wire having a distal end coupled to the proximal end of the expandable treatment member; and
   a flow restrictor carried along the delivery wire at a location that is separate and proximal from the expandable treatment member, the flow restrictor having a body with a distal section and a proximal section, with the body defining an outer surface that extends from the proximal section to the distal section, and a distal mouth at the distal section, the flow restrictor assuming an expanded configuration and an unexpanded configuration, wherein the outer surface of the distal section is circumferentially covered by a biocompatible polymer coating in a manner such that the distal mouth is uncovered, and the outer surface of the proximal section is uncovered, in both the expanded and unexpanded configurations.

2. The device of claim 1, wherein the uncovered proximal section has a smaller diameter than the covered distal section.

3. The device of claim 2, wherein the uncovered proximal section is tapered and the covered distal section is cylindrical.

4. The device of claim 1, wherein the expandable treatment member is configured to define a catch basket.

5. The device of claim 1, wherein the expandable treatment member is moveable relative to the flow restrictor.

6. The device of claim 1, wherein the expandable treatment member is retractable into the distal section of the flow restrictor.

* * * * *